US008916188B2

(12) United States Patent
Trollsas et al.

(10) Patent No.: US 8,916,188 B2
(45) Date of Patent: Dec. 23, 2014

(54) BLOCK COPOLYMER COMPRISING AT LEAST ONE POLYESTER BLOCK AND A POLY (ETHYLENE GLYCOL) BLOCK

(75) Inventors: Mikael O. Trollsas, San Jose, CA (US); Michael H. Ngo, San Jose, CA (US); Syed Hossainy, Fremont, CA (US); David J. Sherman, Tarzana, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 951 days.

(21) Appl. No.: 12/106,212

(22) Filed: Apr. 18, 2008

(65) Prior Publication Data
US 2009/0263457 A1 Oct. 22, 2009

(51) Int. Cl.
A61K 9/00 (2006.01)
A61L 31/10 (2006.01)
A61L 31/16 (2006.01)

(52) U.S. Cl.
CPC ............... A61L 13/148 (2013.01); A61L 31/10 (2013.01); A61L 31/16 (2013.01); A61L 2300/416 (2013.01); A61L 2300/606 (2013.01)
USPC ........................................................ 424/426

(58) Field of Classification Search
None
See application file for complete search history.

(56) References Cited

U.S. PATENT DOCUMENTS

| | | | |
|---|---|---|---|
| 5,272,012 | A | 12/1993 | Opolski |
| 5,702,717 | A * | 12/1997 | Cha et al. ...................... 424/425 |
| 5,702,754 | A | 12/1997 | Zhong |
| 5,997,517 | A | 12/1999 | Whitbourne |
| 6,001,117 | A | 12/1999 | Huxel et al. |
| 6,110,483 | A | 8/2000 | Whitbourne et al. |
| 6,117,949 | A | 9/2000 | Rathi et al. |
| 6,201,072 | B1 | 3/2001 | Rathi et al. |
| 6,274,164 | B1 | 8/2001 | Novich |
| 6,306,176 | B1 | 10/2001 | Whitbourne |
| 6,494,862 | B1 | 12/2002 | Ray et al. |
| 6,500,549 | B1 | 12/2002 | Deppisch et al. |
| 6,503,538 | B1 | 1/2003 | Chu et al. |
| 6,544,223 | B1 | 4/2003 | Kokish |
| 6,544,543 | B1 | 4/2003 | Buchk et al. |
| 6,656,216 | B1 | 12/2003 | Hossainy |
| 6,656,506 | B1 | 12/2003 | Wu et al. |
| 6,663,662 | B2 | 12/2003 | Pacetti et al. |
| 6,663,880 | B1 | 12/2003 | Roorda et al. |
| 6,673,154 | B1 | 1/2004 | Pacetti et al. |
| 6,703,040 | B2 | 3/2004 | Katsarava |
| 6,712,845 | B2 | 3/2004 | Hossainy |
| 6,743,462 | B1 | 6/2004 | Pacetti |
| 6,753,071 | B1 | 6/2004 | Pacetti |
| 6,758,859 | B1 | 7/2004 | Kenny |
| 6,780,424 | B2 * | 8/2004 | Claude ........................... 424/423 |
| 6,790,228 | B2 | 9/2004 | Hossainy |
| 6,818,063 | B1 | 11/2004 | Kerrigan |
| 6,824,559 | B2 | 11/2004 | Michal |
| 6,841,617 | B2 | 1/2005 | Jeong et al. |
| 6,916,788 | B2 | 7/2005 | Seo et al. |
| 6,918,929 | B2 | 7/2005 | Udipi et al. |
| 6,926,919 | B1 | 8/2005 | Hossainy et al. |
| 6,972,054 | B2 | 12/2005 | Kerrigan |
| 7,005,137 | B1 | 2/2006 | Hossainy et al. |
| 7,022,334 | B1 | 4/2006 | Ding |
| 7,056,591 | B1 | 6/2006 | Pacetti et al. |
| 7,060,093 | B2 | 6/2006 | Dang |
| 7,074,276 | B1 | 7/2006 | Sciver et al. |
| 7,115,300 | B1 | 10/2006 | Hossainy et al. |
| 7,135,038 | B1 | 11/2006 | Limon |
| 7,153,520 | B2 | 12/2006 | Seo et al. |
| 7,166,680 | B2 | 1/2007 | Desnoyer |
| 7,169,178 | B1 | 1/2007 | Santos et al. |
| 7,169,404 | B2 | 1/2007 | Hossainy et al. |
| 7,175,874 | B1 | 2/2007 | Pacetti |
| 7,195,640 | B2 | 3/2007 | Falotico et al. |
| 7,201,935 | B1 | 4/2007 | Claude et al. |
| 7,202,325 | B2 | 4/2007 | Hossainy |
| 7,217,426 | B1 | 5/2007 | Hossainy |
| 7,232,490 | B1 | 6/2007 | Hossainy |
| 7,232,573 | B1 | 6/2007 | Ding |
| 7,244,443 | B2 | 7/2007 | Pacetti |
| 7,247,313 | B2 | 7/2007 | Roorda et al. |
| 7,255,891 | B1 | 8/2007 | Pacetti |
| 7,261,946 | B2 | 8/2007 | Claude |
| 7,288,609 | B1 | 10/2007 | Pacetti |
| 7,294,329 | B1 | 11/2007 | Ding |
| 7,311,980 | B1 | 12/2007 | Hossainy et al. |
| 7,323,209 | B1 | 1/2008 | Esbeck et al. |

(Continued)

FOREIGN PATENT DOCUMENTS

| | | |
|---|---|---|
| EP | 1 891 993 | 2/2008 |
| EP | 1 932 551 | 6/2008 |

(Continued)

OTHER PUBLICATIONS

Nair et al. "Polymers as Biomaterials for Tissue Engineering and Controlled Drug Delivery". Adv Biochem/Engin/Biotechnol (2006) 102; 47-90.*
U.S. Appl. No. 09/406,473, Pacetti, filed Sep. 27, 1999
U.S. Appl. No. 10/040,538, Pacetti et al., filed Dec. 28, 2001.
U.S. Appl. No. 10/177,942, Michal et al., filed Jun. 21, 2002.
U.S. Appl. No. 10/316,739, Zhang et al., filed Dec. 10, 2002.
U.S. Appl. No. 10/330,412, Hossainy et al., filed Dec. 27, 2002.
U.S. Appl. No. 10/375,496, Esbeck, filed Feb. 26, 2003.
U.S. Appl. No. 10/376,348, Ding et al., filed Feb. 26, 2003.
U.S. Appl. No. 10/428,691, Pacetti, filed May 1, 2003.
U.S. Appl. No. 10/606,711, Pacetti, filed Jun. 26, 2003.
U.S. Appl. No. 10/705,546, Kwok et al., filed Nov. 10, 2003.
U.S. Appl. No. 10/835,229, Prabhu et al., filed Apr. 28, 2004.
U.S. Appl. No. 10/853,924, Pathak, filed May 25, 2004.
U.S. Appl. No. 10/877,419, Pacetti, filed Jun. 25, 2004.
U.S. Appl. No. 10/883,242, Roorda et al., filed Jun. 30, 2004.
U.S. Appl. No. 10/909,795, Ding et al., filed Jul. 30, 2004.
U.S. Appl. No. 10/913,607, Pacetti et al., filed Aug. 5, 2004.
U.S. Appl. No. 10/976,550, Pacetti et al., filed Oct. 29, 2004.
"Design of Biopharmaceutical Properties through Prodrugs and Analogs", Editor Edward B. Roche, book, 4 title pages (1977).
Harper "Drug Latentiation", Prog. Drug. Res. 4, pp. 221-294 (1962).
Martin et al., "Enhancing the biological activity of immobilized osteopontin using a type—1 collagen affinity coating", Publ. Wiley Periodicals, Inc., pp. 10-19 (2004).
Matyjaszewski et al., "Random, Gradient, and Alternating Copolymers", Handbook of Radical Polymerization Ed. J. Willey&Sons, Inc., pp. 789-790 and 2 title pages, (2002).

(Continued)

Primary Examiner — Robert A Wax
Assistant Examiner — Danah Al-Awadi
(74) Attorney, Agent, or Firm — Squire Patton Boggs (US) LLP

(57) ABSTRACT

The present invention provides a block copolymer for a coating on an implantable device for controlling release of drug and methods of making and using the same.

20 Claims, No Drawings

(56) References Cited

U.S. PATENT DOCUMENTS

| | | | |
|---|---|---|---|
| 7,329,413 B1 | 2/2008 | Pacetti | |
| 7,335,265 B1 | 2/2008 | Hossainy | |
| 7,335,391 B1 | 2/2008 | Pacetti | |
| 7,341,630 B1 | 3/2008 | Pacetti | |
| 7,354,480 B1 | 4/2008 | Kokish et al. | |
| 7,378,106 B2 | 5/2008 | Hossainy et al. | |
| 7,390,524 B1 | 6/2008 | Chen | |
| 7,396,539 B1 | 7/2008 | Hossainy et al. | |
| 7,431,959 B1 | 10/2008 | Dehnad | |
| 7,537,607 B2 * | 5/2009 | Gerberding | 623/1.15 |
| 7,807,211 B2 | 10/2010 | Hossainy et al. | |
| 7,951,194 B2 | 5/2011 | Gueriguian et al. | |
| 8,642,062 B2 | 2/2014 | Trollsas et al. | |
| 2003/0073961 A1 | 4/2003 | Happ | |
| 2003/0104028 A1 | 6/2003 | Hossainy et al. | |
| 2003/0105518 A1 | 6/2003 | Dutta | |
| 2003/0125800 A1 | 7/2003 | Shulze et al. | |
| 2003/0158517 A1 | 8/2003 | Kokish | |
| 2003/0190406 A1 | 10/2003 | Hossainy | |
| 2004/0001872 A1 * | 1/2004 | Shih et al. | 424/426 |
| 2004/0047980 A1 | 3/2004 | Pacetti | |
| 2004/0052858 A1 | 3/2004 | Wu et al. | |
| 2004/0054104 A1 | 3/2004 | Pacetti | |
| 2004/0060508 A1 | 4/2004 | Pacetti | |
| 2004/0062853 A1 | 4/2004 | Pacetti et al. | |
| 2004/0063805 A1 | 4/2004 | Hossainy | |
| 2004/0071861 A1 | 4/2004 | Mandrusov | |
| 2004/0072922 A1 | 4/2004 | Hossainy | |
| 2004/0073298 A1 | 4/2004 | Hossainy | |
| 2004/0086542 A1 | 5/2004 | Hossainy | |
| 2004/0106987 A1 | 6/2004 | Palasis et al. | |
| 2004/0142015 A1 | 7/2004 | Hossainy et al. | |
| 2004/0162609 A1 | 8/2004 | Hossainy et al. | |
| 2004/0180132 A1 | 9/2004 | Pacetti | |
| 2004/0182312 A1 | 9/2004 | Pacetti et al. | |
| 2004/0191405 A1 | 9/2004 | Kerrigan | |
| 2004/0199241 A1 | 10/2004 | Gravett et al. | |
| 2004/0253203 A1 | 12/2004 | Hossainy | |
| 2005/0020734 A1 | 1/2005 | Asgarzadeh et al. | |
| 2005/0021127 A1 | 1/2005 | Kawula | |
| 2005/0025799 A1 | 2/2005 | Hossainy | |
| 2005/0074544 A1 | 4/2005 | Pacetti et al. | |
| 2005/0112170 A1 | 5/2005 | Hossainy et al. | |
| 2005/0112171 A1 | 5/2005 | Tang et al. | |
| 2005/0118344 A1 | 6/2005 | Pacetti | |
| 2005/0137381 A1 | 6/2005 | Pacetti | |
| 2005/0147647 A1 | 7/2005 | Galuser et al. | |
| 2005/0169957 A1 | 8/2005 | Hossainy | |
| 2005/0175666 A1 | 8/2005 | Ding | |
| 2005/0208091 A1 | 9/2005 | Pacetti | |
| 2005/0214339 A1 | 9/2005 | Tang et al. | |
| 2005/0226991 A1 | 10/2005 | Hossainy et al. | |
| 2005/0244363 A1 | 11/2005 | Hossainy et al. | |
| 2005/0265960 A1 * | 12/2005 | Pacetti et al. | 424/78.36 |
| 2005/0271700 A1 | 12/2005 | Desnoyer et al. | |
| 2005/0287184 A1 | 12/2005 | Hossainy et al. | |
| 2006/0002968 A1 | 1/2006 | Stewart et al. | |
| 2006/0034888 A1 | 2/2006 | Pacetti et al. | |
| 2006/0035854 A1 * | 2/2006 | Goldstein et al. | 514/44 |
| 2006/0043650 A1 | 3/2006 | Hossainy et al. | |
| 2006/0047336 A1 | 3/2006 | Gale et al. | |
| 2006/0062824 A1 | 3/2006 | Pacetti et al. | |
| 2006/0089485 A1 | 4/2006 | Desnoyer et al. | |
| 2006/0095122 A1 | 5/2006 | Pacetti | |
| 2006/0115449 A1 | 6/2006 | Pacetti | |
| 2006/0134165 A1 | 6/2006 | Pacetti | |
| 2006/0136048 A1 | 6/2006 | Pacetti et al. | |
| 2006/0246108 A1 | 11/2006 | Pacetti et al. | |
| 2007/0026043 A1 | 2/2007 | Guan et al. | |
| 2007/0032855 A1 | 2/2007 | Hossainy et al. | |
| 2007/0141112 A1 | 6/2007 | Falotico et al. | |
| 2007/0155906 A1 * | 7/2007 | Hissink et al. | 525/242 |
| 2007/0233219 A1 | 10/2007 | Shafi et al. | |
| 2008/0008739 A1 * | 1/2008 | Hossainy et al. | 424/426 |
| 2008/0051872 A1 | 2/2008 | Borck | |
| 2008/0107704 A1 * | 5/2008 | Guo | 424/423 |
| 2008/0145393 A1 | 6/2008 | Trollsas et al. | |
| 2008/0147175 A1 | 6/2008 | Krivoruchko et al. | |
| 2008/0175882 A1 | 7/2008 | Trollsas et al. | |
| 2008/0206307 A1 | 8/2008 | Hossainy et al. | |
| 2008/0248098 A1 | 10/2008 | Jin et al. | |
| 2009/0047322 A1 | 2/2009 | Vange et al. | |
| 2009/0110713 A1 | 4/2009 | Lim et al. | |
| 2009/0285873 A1 | 11/2009 | Lim et al. | |
| 2009/0297584 A1 | 12/2009 | Lim et al. | |
| 2010/0063585 A1 | 3/2010 | Hoffmann et al. | |
| 2013/0230564 A1 | 9/2013 | Kleiner et al. | |
| 2014/0127279 A1 | 5/2014 | Trollsas et al. | |

FOREIGN PATENT DOCUMENTS

| | | | |
|---|---|---|---|
| JP | 58-118763 | 7/1983 | |
| JP | 09-253192 | 9/1997 | |
| JP | 2002-524207 | 8/2002 | |
| WO | WO 99/18142 | 4/1999 | |
| WO | WO 02/100453 | 12/2002 | |
| WO | WO 03/039612 | 5/2003 | |
| WO | WO 03/072158 | 9/2003 | |
| WO | WO 2004/045549 | 6/2004 | |
| WO | WO 2005/000939 | 1/2005 | |
| WO | WO 2005/051449 | 6/2005 | * |
| WO | WO 2007/109069 | 9/2007 | |
| WO | WO 2007/139931 | 12/2007 | |
| WO | WO 2008/121508 | 10/2008 | |
| WO | WO 2009/058694 | 5/2009 | |
| WO | WO 2009/129503 | 10/2009 | |
| WO | WO 2009/148926 | 12/2009 | |
| WO | WO 2010/021883 | 2/2010 | |

OTHER PUBLICATIONS

Serruys et al., "A Randomized Comparison of the Value of Additional Stenting After Optimal Balloon Angioplasty for Long Coronary Lesions", J. of the Am. College of Cardiology vol. 39, No. 3, pp. 393-399 (2002).

Sinkula et al., "Rationale for Design of Biologically Reversible Drug Derivatives: Prodrugs", J. of Pharm. Sciences vol. 64, No. 2, pp. 181-210 (1975).

Spagnuolo et al., "Gas1 is induced by VE-cadherin and vascular endothelial growth factor and inhibits endothelial cell apoptosis", Blood, vol. 103, No. 8, pp. 3005-30012 (2004).

Stella et al., "Prodrugs, Do they have Advantages in clinical Practice?", Drugs 29, pp. 455-473 (1985).

Völkel et al., "Targeting of immunoliposomes to endothelial cells using a single-chain Fv fragment directed against human endoglin (CD105)", Biochimica et Biophysica Acta 1663, pp. 158-166 (2004).

International Search Report for PCT/US2009/041031, mailed Jul. 30, 2010, 15 pgs.

International Search Report for PCT/US2009/054533, mailed Aug. 3, 2010, 15 pgs.

International Search Report for PCT/US2009/053476, mailed Aug. 6, 2010, 17 pgs.

Jeong et al. "Drug release from biodegradable injectable thermosensitive hydrogel of PEG-PLGA-PEG triblock copolymers", J. of Controlled Release 63, pp. 155-163 (2000).

Frost Megan et al. "Preparation and characterization of implantable sensors with nitric oxide release coatings." Microchemical Journal, vol. 74, No. 3, pp. 277-288 (2003).

Meijer et al. "Observations of the bone activity adjacent to unloaded dental implants coated with Polyactive or HA", Journal of Oral Rehabilitation, vol. 22, No. 3, pp. 167-174 (1995).

Sakkers et al. "Assessment of bioactivity for orthopedic coatings in a gap-healing model", Journal of Biomedical Materials Research vol. 36, No. 2, pp. 265-273 (1997).

Cai et al., "Synthesis and Characterization of Polycaprolactone (B)-Poly(lactide-co-glycolide) (A) ABA Block Copolymer", Polymers for Advanced Technologies, 11, pp. 159-166 (2000).

Sawhney et al., "Rapdly degraded terpolymers of dl-lactide, glycolide and e-caprolactone with increased hydrophilicity by copolymerization with polyethers", Journal of Biomedical Materials Research, vol. 24, pp. 1397-1411 (1990).

(56) References Cited

OTHER PUBLICATIONS

Tollon Fabrication of Coated Biodegradable Polymer Scaffolds and Their Effects on Murine Embryonic Stem Cells, University of Florida, pp. 1-5 (2005).
Waksman "Biodegradable Stents: They do their job and disappear" Journal of Invasive Cardiology, vol. 18, issue 2, pp. 1-8 (2006).
U.S. Appl. No. 11/870,393, Kleiner et al., filed Oct. 10, 2007.
Astete, Carlos E., and Cristina M. Sabliov, *J. Biomater. Sci. Polymer Ed.*, vol. 17, No. 3, pp. 247-289 (2006).
Jain Rajeev A. "The Manufacturing Techniques of Various Drug Loaded Biodegradable poly(lactide-co-glycolide) (PLGA) devices," *Biomaterials*: 21(2000), p. 2475-2490.

\* cited by examiner

BLOCK COPOLYMER COMPRISING AT LEAST ONE POLYESTER BLOCK AND A POLY (ETHYLENE GLYCOL) BLOCK

FIELD OF THE INVENTION

The present invention relates to a block copolymer comprising at least one polyester block(s) and a poly(ethylene glycol) block for controlling the release of a drug from a coating for an implantable device.

BACKGROUND OF THE INVENTION

Percutaneous coronary intervention (PCI) is a procedure for treating heart disease. A catheter assembly having a balloon portion is introduced percutaneously into the cardiovascular system of a patient via the radial, brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug delivery stents. For example, release of a drug from a coating formed of an amorphous may often have a burst release of the drug, resulting in insufficient control release of the drug.

Therefore, there is a need for a coating that provides for a controlled release of a drug in the coating.

The embodiments of the present invention address the above-identified needs and issues.

SUMMARY OF THE INVENTION

In according to one aspect of the present invention, it is provided an implantable device. The implantable device comprises a block copolymer that comprises at least one polyester block and at least one poly(ethylene glycol) (PEG) block. The PEG block has a weight average molecular weight ($M_w$) from about 1,000 Daltons to about 30,000 Daltons. The block copolymer is biosoluble, and upon exposure to a physiological environment, 80% mass of the block copolymer will dissolve in a period of about 1 day to about 90 days.

In some embodiments, the polyester block(s) in the block copolymer comprises glycolide, lactide, trimethylene carbonate, caprolactone, or combinations thereof. The lactide can be optically active or racemic and can be D,L-lactide, L-lactide, D-lactide, or combinations thereof. The polyester block(s) can have various molar concentrations of any of these monomers. For example, the polyester block(s) can have lactide with a molar concentration in the polyester block(s) of at least 60% or at least 80%. In some embodiments, the polyester block(s) can have glycolide with a molar concentration in the polyester block(s) of between about 10% and about 75%.

In some embodiments, the block copolymer can comprise biodegradable side blocks. The side blocks can be any biodegradable polymer, a few examples of which are polyanhydrides, poly(ester amides), polythioesters, or combinations thereof.

In some embodiments, the block copolymer can be an alternating A-B block copolymer where A is a poly(lactide-co-glycolide) (PLGA) block and B is the PEG block.

A few non-limiting examples of the block copolymer are poly(lactide-co-glycolide-co-caprolactone)-block-PEG-poly(lactide-co-glycolide-co-caprolactone), poly(trimethylene carbonate-co-glycolide)-block-PEG-block-poly(trimethylene carbonate-co-glycolide), polylactide-block-PEG-polyactide, poly(trimethylene carbonate-co-glycolide)-block-PEG-poly(trimethylene carbonate-co-glycolide), and combinations thereof.

The block copolymer of embodiments described above can have different molecular weights. In some embodiments, the block copolymer has a weight-average molecular weight ($M_w$) of about 60,000 Daltons or higher or a $M_w$ of about 100,000 Daltons or higher.

The block copolymer of the various embodiments above can form a coating on the implantable device or at least a portion of the body structure of the implantable device. In some embodiments, the coating or the body structure of the implantable device can further comprise a bioactive agent. Some examples of the bioactive agent can be paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), γ-hiridun, clobetasol, pimecrolimus, imatinib mesylate, midostaurin, feno fibrate, prodrugs thereof, co-drugs thereof, and combinations thereof.

The implantable device can be any implantable device such as a stent. The implantable device can be biodurable or bioabsorbable. In some embodiments, the implantable device is a bioabsorbable stent.

In according to a further aspect of the present invention, it is provided a method of fabricating an implantable medical device. The method comprises forming a coating on the implantable device, the coating comprising a block copolymer of the various embodiments described above. The coating can comprise crystalline, amorphous, or semi-crystalline morphologies. In some embodiments, the coating comprises a semi-crystalline morphology where the block copolymer comprises polyester block(s) having lactide in a molar concentration of at least 60% or at least 80%.

The implantable device described herein can be formed on an implantable device such as a stent, which can be implanted in a patient to treat, prevent, mitigate, or reduce a vascular medical condition, or to provide a pro-healing effect.

In some embodiments, the vascular medical condition or vascular condition is a coronary artery disease (CAD) and/or a peripheral vascular disease (PVD). Some examples of such vascular medical diseases are restenosis and/or atherosclerosis.

Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, or combinations of these.

DETAILED DESCRIPTION

The present invention provides a block copolymer comprising a poly(ethylene glycol) (PEG) block and at least one polyester block. The block copolymer can form a coating on an implantable device for controlling the release of a drug from the coating. The polyester block is hydrophobic, imparting hydrophobicity to the block copolymer; and the PEG block is hydrophilic, imparting hydrophilicity to the block copolymer. The block copolymer generally has a weight-average molecular weight ($M_w$) of about 60,000 Daltons or higher or, more preferably, about 100,000 Daltons or higher.

The polyester block can include any monomers capable of forming the polyester block. In some embodiments, the polyester block(s) can include units such as lactide, glycolide, caprolactone, trimethylene carbonate (TMC), or combinations thereof. Selection of different monomers for the polyester block(s) allows one to design the molecular structure of the blocks such that the drug/polymer interaction parameter can be minimized to provide for a better control of the drug release. A drug/polymer interaction parameter is directly and positively related to the difference between the solubility of drug and polymer. For the drug to have a controlled release from the polymers, the drug and the polymer should be miscible, which means their interaction parameter is equal to zero. The miscibility of the drug and polymer can be estimated by the Hildebrand solubility parameters, and therefore, the Hildebrand solubility parameters of the drug and polymer provide a measurement of the drug/polymer interaction parameter. For example, to provide a controlled release of everolimus from a coating formed of a polyester including PLLA and/or PLGA, the polyester block(s) can be designed to include hydrophobic units such as caprolactone units; PLLA or PLGA are more hydrophilic compared to everolimus, and it's desirable to have a more hydrophobic chain of caprolactone so that the polymer would be more hydrophobic to be more miscible with drug.

In some embodiments, the block copolymer comprises at least one polyester block comprising glycolide and a PEG block. The glycolide provides an accelerated or enhanced degradation of the block copolymer. For example, the block copolymer can comprises polyester blocks derived from lactide and glycolide and a PEG block where the glycolide monomer imparts enhanced degradation to the polymer, and the lactide monomer imparts mechanical strength to the block copolymer. For faster degradation, the polyester blocks generally have a molar concentration of glycolide between about 10% and about 75%.

The block copolymer disclosed herein can have various absorption rate. For example, the block copolymer can have an absorption rate that about 80% mass of the block copolymer can dissolve in a period of about 1 day to about 90 days in a physiological environment. A coating formed of such a block copolymer is preferable to be biosoluble. Such biosoluble coatings will absorb in the blood stream by dissolving mechanism thereby mitigating side effects caused by smaller molecule by-products, which can cause inflammation or other adverse reaction to the vessel wall, produced in the absorption or degradation process of a polymer in a coating.

In the block copolymer where the polyester block comprises lactide monomer, the lactide can be DL-lactide, D-lactide, L-lactide, or meso-lactide. Such a block copolymer can form a coating with a semi-crystalline morphology where the L-lactide molar concentration can be at least 60% of the polyester block(s), e.g., more than 80% of the polyester block(s).

The PEG block also imparts biobeneficial properties to the block copolymer. As used herein, the term "biobeneficial" shall mean, among others, the attributes of being non-fouling and inflammation reduction. Such attributes also include biosoluble. As used herein, the term biosoluble refers to the attribute of being absorbable in the blood stream by dissolving mechanism.

In the block copolymer, the $M_w$ of the PEG block generally can range from about 1K Daltons to about 30K Daltons. In some embodiments, the $M_w$ of the PEG block can be below 1K Daltons or above 30K Daltons. However, the molecular weight of the PEG block shall be small enough (e.g., below about 40,000 Daltons) such that the block copolymer can degrades into fragments capable of passing through the kidney membrane. Some exemplary $M_w$ of the PEG block are 6,000 Daltons, 10,000 Daltons, 20,000 Daltons, or 25,000 Daltons. The block copolymer can have various levels of PEG.

In some embodiments, the block copolymer described herein can include side blocks. To avoid a build up of the polymers in the kidneys, the side blocks can be designed to be biodegradable. Some examples of the side blocks are polyanhydrides, poly(ester amide), polyamino acids, peptides, and/or polythioesters.

Some examples of the block copolymers are PLGA-PEG-PLGA, P(LA-GA-CL)-PEG-P(LA-GA-CL), P(TMC-GA)-PEG-P(TMC-GA), PLA-PEG-PLA, P(TMC-GA)-PEG-P(TMC-GA). As used herein, "LA" is lactide, "GA" is glycolide, "LGA" is lactide-co-glycolide, "CL" is caprolactone, and TMC is trimethylene carbonate.

In some embodiments, the block copolymer can be an alternating block copolymer. For example, the block copolymer is A-B alternating block copolymer where the A block is PLGA and the B block is PEG.

In some embodiments, the block copolymer can form a coating that can include one or more bioactive agents, e.g., drug(s). Some exemplary bioactive agents that can be included in a coating having a hygroscopic layer described above are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), γ-hiridun, clobetasol, pimecrolimus, imatinib mesylate, midostaurin, cRGD, fenofibrate, prodrugs thereof, co-drugs thereof, and combinations thereof. Some other examples of the bioactive agent include siRNA and/or other oligoneucleotides that inhibit endothelial cell migration. Some further examples of the bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. As used herein, in some embodiments, the term "drug" and the term "bioactive agent" are used interchangeably.

A coating formed from a block copolymer described herein can be formed on an implantable device such as a stent, which can be implanted in a patient to treat, prevent, mitigate, or reduce a vascular medical condition, or to provide a prohealing effect.

In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, or combinations of these.

DEFINITIONS

Wherever applicable, the definitions to some terms used throughout the description of the present invention as provided below shall apply. The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 K Daltons) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a durable polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prod rug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.,* 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.,* 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs,* 29: 455-473 (1985).

Unless otherwise specifically defined, the terms "polymer" and "polymeric" refer to compounds that are the product of a polymerization reaction. These terms are inclusive of homopolymers (i.e., polymers obtained by polymerizing one type of monomer by either chain or condensation polymers), copolymers (i.e., polymers obtained by polymerizing two or more different types of monomers by either chain or condensation polymers), condensation polymers (polymers made from condensation polymerization, tri-block copolymers, etc., including random (by either chain or condensation polymers), alternating (by either chain or condensation polymers), block (by either chain or condensation polymers), graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

As used herein, the term "crystalline" refers to having crystallinity of more than 5% in a tri-block copolymer. In some embodiments, the term "crystalline" can refer to having crystallinity of more than about 10%, more than about 20%, more than about 30%, more than about 40%, more than about 50%, or more than about 60% in a tri-block copolymer.

The term "semi-crystalline morphology" refers to having crystalline domain(s)/region(s) and amorphous domain(s)/region(s) in a polymer.

Tri-block copolymers with different contents of these three monomers have different properties with regard to, e.g., rate of degradation, mechanical properties, drug permeability, water permeability, and drug release rate, depending on a particular composition of the monomers in the tri-block copolymer.

In some embodiments, the tri-block copolymer can have a $T_g$ below about 60° C. This tri-block copolymer can have units derived from D-lactide, L-lactide, or D,L-lactide from about 10% to about 80% by weight. Monomers such as D-lactide, L-lactide, glycolide, and dioxanone can crystallize if present in high concentration in a polymer. However, crystallization of units from any of these monomers can be minimized or prevented if concentration of each is below 80% by weight in the polymer. Therefore, the composition of a tri-block copolymer described herein shall include units of D-lactide or L-lactide at about 10-80% by weight, units of glycolide at about 5-80% by weight and units from the third, low $T_g$ monomer at about 5-60% by weight. The tri-block copolymer can have a weight-average molecular weight ($M_w$) of about 10K Daltons or above, preferably from about 20K Daltons to about 600K Daltons.

Ratios of units from the lactide, glycolide and the low $T_g$ monomers can vary, forming a tri-block copolymer having different properties, e.g., different degradation rates, different rates of release of a drug from a coating formed of the tri-block copolymer, different drug permeability, different flexibility or mechanical properties. As noted above, generally, the glycolide provides an accelerated or enhanced degradation of the tri-block copolymer, the lactide monomer provides mechanical strength to the tri-block copolymer, and the third, low $T_g$ monomer can enhance drug permeability, water permeability, and enhancing degradation rate of the polymer, imparting greater flexibility and elongation, and improving mechanical properties of a coating formed of the tri-block copolymer.

In some embodiments, the ratio of the various monomers can vary along the chain of the tri-block copolymer. In such a tri-block copolymer, one point of the chain of polymer can be heavy with one monomer while another point of the chain can be light with the same monomer, for example. If a monofunctional initiator is used, and if the selected monomers have highly different reactivity ratios, then a gradient of composition is generated as the monomers are consumed during the polymerization. In another methodology, such a tri-block copolymer can be prepared by so-called gradient polymerization wherein during the polymerization a first or second monomer is progressively added to the reactor containing all, or a portion of, the first monomer. (Matyjaszewski K. and Davis T. P. eds. Handbook of Radical Polymerization, John Wiley & Sons, 2002, p. 789). Yet a third method is by introducing blocks of various ratios of the monomers into the chain of the tri-block copolymer.

In some embodiments, the block copolymer described herein can be used to build one or more blocks in combination with other blocks of biodegradable or biodurable polymers described below.

Preparation of the Block Copolymer Described Herein can be Readily accomplished by established methods of polymer synthesis. For example, PLGA-PEG-PLGA can be synthesized by using PEG as an initiator for the ring-opening polymerization of D,L-lactide and glycolide in the presence of stannous octoate as a catalyst.

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogs of rapamycin, structural derivatives and functional analogs of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O—[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), Biolimus A9 (Biosensors International, Singapore), AP23572 (Ariad Pharmaceuticals), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™(bivalirudin, from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6, 6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind, and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A: 10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O—[2-(2-hydroxy)ethoxy]ethyl-rapamycin, 40-O-tetrazole-rapamycin, 40-epi-(N1-tetrazolyl)-rapamycin (zotarolimus), Biolimus A9 (Biosensors International, Singapore), AP23572 (Ariad Pharmaceuticals), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

An alternative class of drugs would be p-para-α-agonists for increased lipid transportation, examples include feno fibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can include a block copolymer described herein in a layer according to any design of a coating. The coating can be a multi-layer structure that includes at least one reservoir layer, which is layer (2) described below, and can include any of the following (1), (3), (4) and (5) layers or combination thereof:

(1) a primer layer; (optional)
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer") (optional);
(4) a topcoat layer; and/or (optional);
(5) a finishing coat layer. (optional).

In some embodiments, a coating of the invention can include two or more reservoir layers described above, each of which can include a bioactive agent described herein.

Each layer of a stent coating can be disposed over the implantable device (e.g., a stent) by dissolving the amorphous polymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C., e.g., 80° C., for a period of time between about 5 minutes and about 60 minutes, if desired, to allow for crystallization of the polymer coating, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied directly or indirectly over at least a portion of the stent surface to serve as a reservoir for at least one bioactive agent (e.g., drug) that is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, and irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through the amorphous polymeric layer(s) into a blood vessel or tissue.

In one embodiment, any or all of the layers of the stent coating can be made of a block copolymer described herein. In another embodiment, the outermost layer of the coating can be limited to a block copolymer as defined above.

To illustrate in more detail, in a stent coating having all four layers described above (i.e., the primer, the reservoir layer, the topcoat layer and the finishing coat layer), the outermost layer is the finishing coat layer, which can be made of a block copolymer described. The remaining layers (i.e., the primer, the reservoir layer and the topcoat layer) optionally having the properties of being biodegradable or, biostable, or being mixed with a block copolymer as described herein. The polymer(s) in a particular layer may be the same as or different than those in any of the other layers, as long as the layer on the outside of another bioabsorbable should preferably also be bioabsorbable and degrade at a similar or faster relative to the inner layer. As another illustration, the coating can include a single matrix layer comprising a polymer described herein and a drug.

If a finishing coat layer is not used, the topcoat layer can be the outermost layer and should be made of a block copolymer as described. In this case, the remaining layers (i.e., the primer and the reservoir layer) optionally can also be fabricated of a block copolymer described herein. The polymer(s) in a particular layer may be the same as or different than those in any of the other layers, as long as the outside of another bioabsorbable should preferably also be bioabsorbable and degrade at a similar or faster relative to the inner layer.

If neither a finishing coat layer nor a topcoat layer is used, the stent coating could have only two layers—the primer and the reservoir. In such a case, the reservoir is the outermost layer of the stent coating and should be made of a block copolymer described. The primer optionally can also be fabricated of a block copolymer described herein and optionally one or more biodegradable polymer(s), biostable polymer(s), or a combination thereof. The two layers may be made from the same or different polymers, as long as the layer on the outside of another bioabsorbable should preferably also be bioabsorbable and degrade at a similar or faster relative to the inner layer.

Any layer of a coating can contain any amount of a block copolymer described herein and optionally being mixed with another bioabsorbable and/or biocompatible polymer. Non-limiting examples of bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Any layer of a coating can also contain any amount of a non-degradable polymer, or a blend of more than one such. When a non-degradable polymer is used, the non-degradable polymer shall have a molecular weight ($M_w$) of about 40K Daltons or below. In general since not many polymers are very elastic enough. If they are not, the higher Mw will provide the toughness for the coating, ideally in drug eluting stents, polymers of higher than 100 kD are preferable. Also, since they are not degradable or soluble, clearing the kidney should not be a concern. Non-limiting examples of non-degradable polymers include poly(methyl methacrylate), poly(ethyl methacrylate), poly(butyl methacrylate), poly(2-ethylhexyl methacrylate), poly(lauryl methacrylate), poly(2-hydroxylethyl methacrylate), poly(ethylene glycol (PEG) acrylate), poly(PEG methacrylate), methacrylate polymers containing 2-methacryloyloxyethylphosphorylcholine (MPC), PC1036, and poly(n-vinyl pyrrolidone, poly(methacrylic acid), poly(acrylic acid), poly(hydroxypropyl methacrylate), poly(hydroxypropyl methacrylamide), methacrylate polymers containing 3-trimethylsilylpropyl methacrylate, and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a block copolymer described herein, optionally with one or more other biodegradable or biostable polymer or copolymers.

Under the method, a portion of the implantable device or the whole device itself can be formed of the material containing a biodegradable or biostable polymer or copolymer. The method can deposit a coating having a range of thickness over an implantable device. In certain embodiments, the method deposits over at least a portion of the implantable device a coating that has a thickness of ≤about 30 micron, or ≤about 20 micron, or ≤about 10 micron, or ≤about 5 micron.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Non-limiting examples of polymers, which may or may not be the block copolymers defined above, that can be used to fabricate an implantable device include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(D-lactic acid-co-glycolide-co-caprolactone) (PDLA-GA-CL), poly(L-lactic acid-co-glycolide-co-caprolactone) (PLLA-GA-CL), poly(DL-lactic acid-co-glycolide-co-caprolactone) (PDLLA-GA-CL), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be suited for fabricating an implantable device include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from ATOFINA Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O—[2-(2-hydroxy)ethoxy]ethyl-rapamycin, 40-O-tetrazole-rapamycin, 40-epi-(N1-tetrazolyl)-rapamycin (zotarolimus), Biolimus A9 (Biosensors International, Singapore), AP23572 (Ariad Pharmaceuticals), pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

The invention claimed is:

1. An implantable device comprising a block copolymer, the block copolymer comprising at least one polyester block and at least one poly(ethylene glycol) (PEG) block,
wherein:
the PEG block has a weight average molecular weight from about 1,000 Daltons to about 30,000 Daltons,
the block copolymer is biosoluble,
upon exposure to a physiological environment, 80% mass of the block copolymer will dissolve in a period of about 1 day to about 90 days; and
the block copolymer comprises biodegradable side blocks, the side blocks being polythioesters or a combination of polyanhydrides and polythioesters.

2. The implantable device of claim 1, wherein the polyester block of the block copolymer comprises D,L-lactide, L-lactide, D-lactide, meso-lactide or a combination thereof.

3. The implantable device of claim 1, wherein the block copolymer forms a coating on the implantable device, the coating comprising a semi-crystalline morphology, and
wherein the polyester block of the block copolymer comprises lactide of a molar concentration of at least 60%.

4. The implantable device of claim 3, wherein the polyester block of the block copolymer comprises lactide of a molar concentration of at least 80%.

5. The implantable device of claim 1, wherein the polyester block of the block copolymer comprises glycolide of a molar concentration between about 10% and about 75%.

6. The implantable device of claim 1, wherein the polyester block of the block copolymer comprises lactide, glycolide, and caprolactone.

7. The implantable device of claim 1, wherein the side blocks of the block copolymer are selected from polythioesters.

8. The implantable device of claim 1, wherein the block copolymer forms a coating on the implantable device.

9. The implantable device of claim 1, wherein the block copolymer forms at least a portion of the body structure of the implantable device.

10. The implantable device of claim 8, wherein the coating further comprises a bioactive agent.

11. The implantable device of claim 10, wherein the bioactive agent is selected from the group consisting of paclitaxel, docetaxel, estradiol, 17-beta-estradiol, nitric oxide donors, super oxide dismutases, 4 amino-2,2,6,6-tetramethylpiperidine-1-oxyl (4-amino-TEMPO), biolimus, tacrolimus, dexamethasone, dexamethasone acetate, corticosteroids, rapamycin, everolimus, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, Biolimus A9, AP23572, γ hiridun, clobetasol, pimecrolimus, imatinib mesylate, midostaurin, cRGD, fenofibrate, and combinations thereof.

12. The implantable device of claim 1, which is a stent.

13. The implantable device of claim 1, which is a bioabsorbable stent.

14. The implantable device of claim 8, which is a stent.

15. The implantable device of claim 9, which is a stent.

16. A method, comprising implanting in a human being an implantable device according to claim 10 for treating, or ameliorating a medical condition selected from the group consisting of restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, and combinations of these.

17. A method, comprising implanting in a human being an implantable device according to claim 11 for treating, or ameliorating a medical condition selected from the group consisting of restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, and combinations of these.

18. The implantable device of claim 8, wherein the coating comprises an outermost coating layer comprising the block copolymer.

19. The implantable device of claim 18, wherein the outermost coating layer consists essentially of the block copolymer.

20. The implantable device of claim 1, wherein the polyester block is formed from trimethylene carbonate and glycolide.

* * * * *